(12) United States Patent
Filsouf

(10) Patent No.: US 6,434,757 B1
(45) Date of Patent: Aug. 20, 2002

(54) FEMALE STANDING URINATION CONE

(76) Inventor: Ehsan Filsouf, 8590 SW. 168 Ter., Miami, FL (US) 33157

( * ) Notice: Subject to any disclaimer, the term of this patent is extended or adjusted under 35 U.S.C. 154(b) by 0 days.

(21) Appl. No.: 09/690,855

(22) Filed: Oct. 18, 2000

(51) Int. Cl.$^7$ ............................................... A47K 11/12
(52) U.S. Cl. ...................... 4/144.2; 4/144.1; 4/144.3; 604/329
(58) Field of Search ............................. 4/144.1, 144.2, 4/144.3, 144.4, 307; 604/329

(56) References Cited

U.S. PATENT DOCUMENTS

| | | |
|---|---|---|
| 3,731,869 A | 5/1973 | Griffin |
| 3,746,240 A | 7/1973 | Flynn |
| 4,305,161 A | 12/1981 | Diaz |
| 4,800,900 A | 1/1989 | French |
| 4,815,151 A | 3/1989 | Ball |
| 5,333,330 A | 8/1994 | Murtagh |
| 5,408,703 A | 4/1995 | Cicio ......................... 4/144.2 |
| 5,605,161 A | 2/1997 | Cross |
| 5,662,630 A | 9/1997 | Raynie |
| 5,966,748 A | 10/1999 | Young et al. ................. 4/144.4 |

FOREIGN PATENT DOCUMENTS

GB    2240717    * 8/1991 ................. 604/329

* cited by examiner

Primary Examiner—Gregory Huson
Assistant Examiner—Kathleen J. Prunner
(74) Attorney, Agent, or Firm—Siemens Patent Services, LC

(57) ABSTRACT

The present invention features a device to facilitate female urination from a standing position. A collapsible structure is readily expanded by pressing on two opposing edges. Once expanded, the device is held in its open state by a unique locking mechanism. Because a user does not need to exert continuous pressure on the device to keep it in an open, operable state, it is easier to use than other similar devices. The device may be cleaned, collapsed and stored for re-use or may be supplied as a single use, disposable unit.

12 Claims, 4 Drawing Sheets

FEMALE STANDING URINATION CONE

BACKGROUND OF THE INVENTION

1. Field of the Invention

The present invention relates to urination devices for women, and more particularly, a device for allowing a woman to urinate in a standing position and discharge the urine at a distance from her body.

2. Description of the Prior Art

For a variety of reasons, it is sometimes desirable for a woman to be able to urinate in a standing position. Restroom conditions are often such that a woman may not want to sit on a public toilet seat, or when traveling or camping facilities are not always available. In these situations, urination is difficult as the flow can not be directed, as it can by a male. Therefore, a means to facilitate urination while in a standing position and directing the flow away from the body is desirable. A number of devices for this purpose have been offered.

U.S. Pat. No. 5,966,748, issued to Edward J. Young on Oct. 19, 1999 presents a TINKLE SAFE, female urinary device, fitted to the female body, which allows a female to urinate in a standing position. Young is presented as either a flat sheet of water resistant material which must be formed as a funnel by the user or as a pre-shaped funnel which makes no provision for being collapsible for storage, other than by merely creasing the cone of the funnel. The present invention, on the other hand is formed in a flattened configuration which is easily opened for use by pressing on an upper and a lower lateral crease to spread its sides.

U.S. Pat. No. 5,408,703, issued to William Cicio on Apr. 25, 1995, presents a FEMALE URINATION AID, a collapsible funnel, formed to the female body to receive urine, while in a standing position, and deposit it at a distance from the female body. Cicio presents a folded funnel, fitted to the contours of the female body, which may be opened for use by pressing simultaneously on an upper and a lower lateral crease. When pressure is released from the upper and lower lateral creases, the funnel naturally tends to return to its folded state. By contrast, the present invention includes a semi-elliptical crease in each side of the funnel and intersecting the lower lateral crease near each end of the funnel such that when the upper and lower lateral creases are pressed simultaneously an arched rib is formed allowing the funnel to retain its shape.

U.S. Pat. No. 5,333,330, issued to Daniel S. Murtagh on Aug. 2, 1994, presents a FEMININE URINARY DEVICE, again a collapsible funnel, formed to the female body to receive urine, while in a standing position, and deposit it at a distance from the female body. Although of a different design, Murtagh also may be opened for use by pressing simultaneously on an upper and a lower lateral crease, and when pressure is released form the upper and lower lateral creases, the funnel naturally tends to return to its folded state. Again, by contrast, the present invention retains its open state due to the arched rib.

U.S. Pat. No. 4,815,151, issued to Dianne M. Ball on Mar. 28, 1989, presents a URINARY GUIDE APPARATUS AND METHOD OF USING THE SAME. Ball is of a molded, shape retaining material, formed to the female body to receive urine, while in a standing position, and deposit it at a distance from the female body. The present invention, on the other hand, folds to a flat configuration for storage.

U.S. Pat. No. 4,305,161, issued to Rudy J. Diaz on Dec. 15, 1981 presents a URINATING AID FOR WOMEN, a disposable, waterproof bag held open by a reusable, rigid, handled frame, into which a woman can urinate from a standing position and then dispose of the bag. By comparison, the present invention allows for direct disposal of the urine.

U.S. Pat. No. 3,746,240, issued to Jerome R. Flynn on Jul. 17, 1973, presents a FOLDED CARDBOARD SPECIMEN CONTAINER OR URINAL, a folded container, opened at one end and containing a liquid impervious bag for containing a urine specimen. While Flynn serves as a method of collecting and holding a urine sample, the present invention provides a means of disposal of urine.

U.S. Pat. No. 3,731,869, issued to Nicholas E. Griffin on May 8, 1973, presents a DISPOSABLE CONTAINER, again a folded container, opened at one end for receiving and containing a urine sample. Griffin also serves as a method of collecting and holding a urine sample, while the present invention provides a means of disposal of urine.

U.S. Pat. No. 5,605,161, issued to Leta K. Cross on Feb. 25, 1997, presents a DISPOSABLE URINALYSIS DEVICE WITH INDICATOR, a device with a substantially rigid upper opening and laterally collapsible by accordion pleats, containing one or more test strips for conducting urinalysis testing. Like the present invention, Cross allows for urination by a woman in a standing position and discharge of the urine at a distance from her body, but the lack of a provision for test strips reduces the cost present invention.

U.S. Pat. No. 5,662,630, issued to Arthur D. Raynie on Sep. 2, 1997, presents a BIODEGRADABLE URINE COLLECTION DEVICE wherein a rigid member for engaging a collection bag with the female body in a standing or sitting position is a rigid funnel like device. While Raynie could be used as a method of receiving urine, while in a standing position, and depositing it at a distance from the female body, the present invention is much more economical in its construction and convenient in its shortage.

None of the above inventions and patents, taken either singly or in combination, is seen to describe the instant invention as claimed.

SUMMARY OF THE INVENTION

For a variety of reasons, it is sometimes desirable for a woman to be able to urinate in a standing position. Restroom conditions are often such that a woman may not want to sit on a public toilet seat, or when traveling or camping facilities are not always available. In these situations, urination is difficult as the flow can not be directed, as it can by a male. Therefore, a means to facilitate urination while in a standing position and directing the flow away from the body is desirable.

Accordingly, it is a principal object of the invention provide a means for a female to urinate in a standing position as is customary for a male and direct the flow away from her body.

It is another object of the invention to provide a means for a female to urinate in a standing position and direct the flow away from her body which is convenient to store and carry.

It is a further object of the invention to provide a means for a female to urinate in a standing position and direct the flow away from her body which is easy to use.

Still another object of the invention is to provide a means for a female to urinate in a standing position and direct the flow away from her body which is sanitary to use.

An additional object of the invention is to provide a means for a female to urinate in a standing position and direct the flow away from her body which is easily disposable.

It is again an object of the invention to provide a means for a female to urinate in a standing position and direct the flow away from her body which is economical to produce.

A further object of the invention is to provide a means for a female to urinate in a standing position and direct the flow away from her body which can be produced of a durable material for repeated use.

It is an object of the invention to provide improved elements and arrangements thereof in an apparatus for the purposes described which is inexpensive, dependable and fully effective in accomplishing its intended purposes.

It is an additional object of the invention to provide a means for a female to urinate in a standing position and direct the flow away from her body without the total removal of outer garments.

Still another object of the invention is to provide a means for a female to urinate in a standing position and direct the flow away from her body by only unzipping her outer garment or pulling her skirt to the side.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

Figure 1:
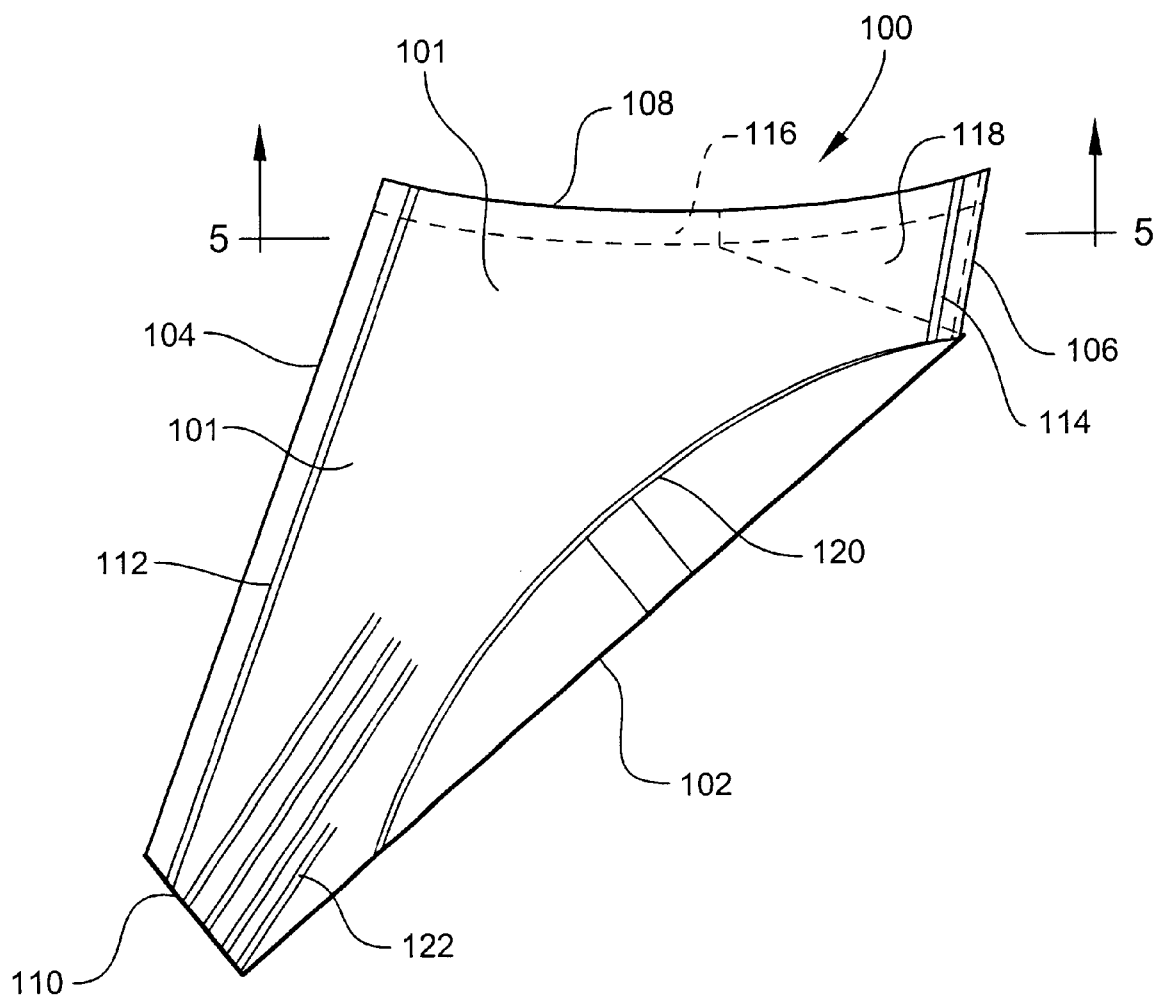
FIG. 1 is a side elevational view of the invention in its folded state.

Referring now to FIG. 1, the invention, cone 100, in its folded state is generally pentagonal in shape. The cone 100 is formed by a pair of substantially planar pentagonal sides each having a top edge 108, a bottom edge 110, an upper right edge 106, a lower right edge 102 and a left edge 104 and formed of material such as water resistant cardboard or paper. The pair of sides are continuously joined one to the other along the upper right edge 106, the lower right edge 102 and the left edge 104 thereby defining an upper right, a lower right and a left hinge line, respectively. The pair of sides are disposed substantially flat and adjacent one another for storage and are movable away from one another to an open, operable position when in use. Each of the sides form a side 101 of cone 100. Edge 102 is formed by a fold, thus creating the sides mentioned above. Edges 104 and 106 are formed by glued flaps formed along the edge of one side 101 and folded over the edge of the second side 101. Each side 101 has score lines 112 and 114 along the edge of the glued flaps. Edge 108 is formed by folding a flap 116 inwardly to form a finished edge while edge 110 is left as a raw cut. The fold at edge 106 is reinforced by reinforcing flap 118, folded and glued to its interior surface. Edge 108 is slightly concave to facilitate a close fit to the female vulva when in use. A semi-elliptical scored line 120 runs from the junction of edge 102 and 106 to a point proximate the junction of edges 102 and 110. A number of center score lines 122 intersect the edge 110 approximately midway between its junction with edges 102 and 104 and generally bisect the area between edges 102 and 104. Center score lines 122 run approximately ¼ the length of cone 100 and run from a central region of and substantially perpendicular to the bottom edge of the pair of sides.

Figure 2:
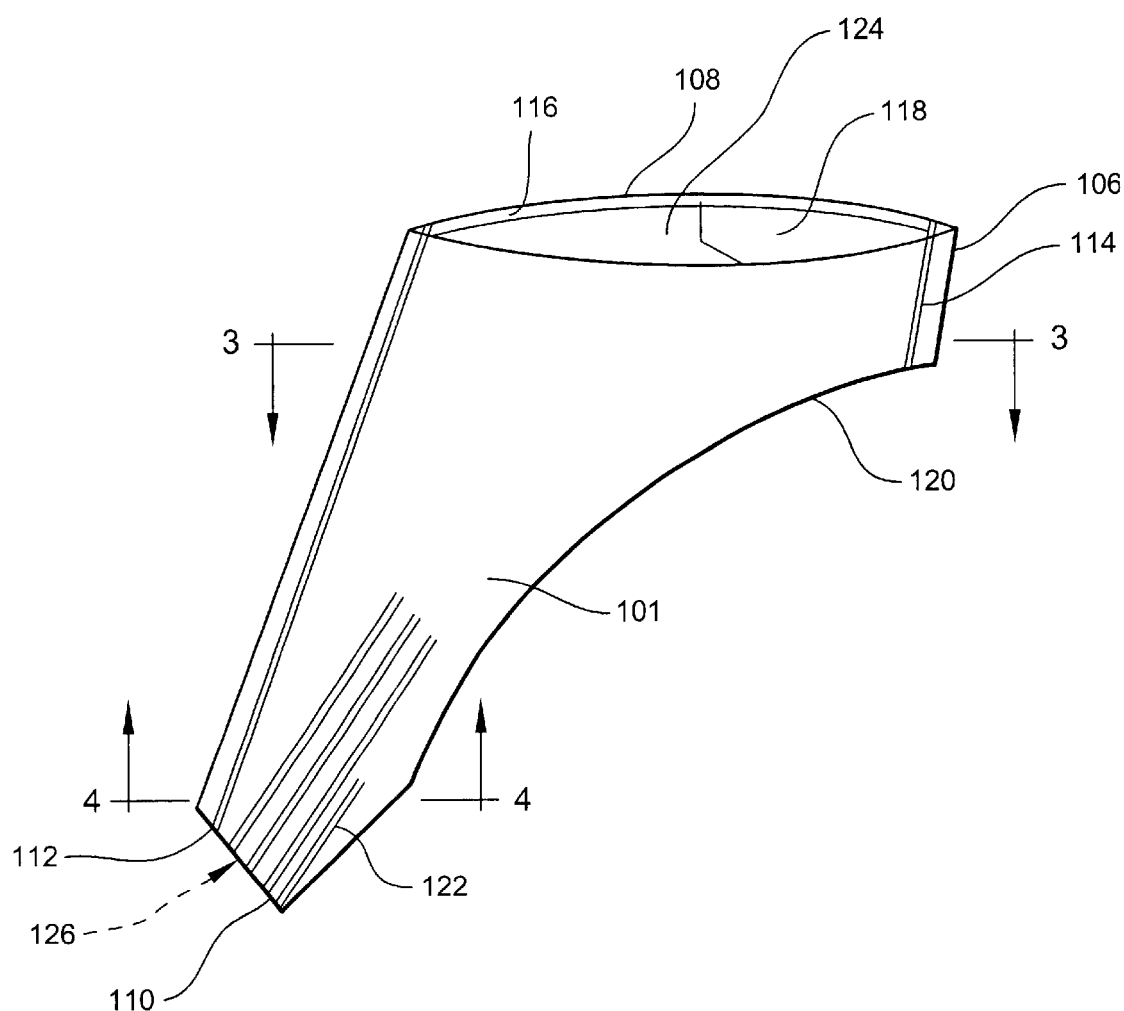
FIG. 2 is an environmental perspective view of the invention, from above, in its open state.

FIG. 2 presents cone 100 in its open state, which is achieved by simultaneously pressing edges 102 and 104 of FIG. 1. In so pressing on edges 102 and 104, score lines 112, 114, 120 and center score lines 122 allow the two sides 101 to flex away from each other while the semi-elliptical curve of score line 120 allows it to lock forming a semi-rigid, arching lower surface to cone 100 holding it in an open position, thus creating upper opening 124 and lower opening 126. Score line 120 forms a means for releasably locking the pair of sides in the open, operable position and is hingedly connected along the lower right hinge line. The open, operable position defines a hollow structure having the semi-elliptical opening 124 proximate the top edge 108 adapted to enclose a female user's vulva for receiving urine. The lower opening 126 is proximate the bottom edges I 10 of the pair of sides for discharging urine. The scored lines 120 have a first terminus proximate a juncture of the upper right edge 106 and the lower right edge 102, and a second terminus located along the lower right edge 102. The second terminus is disposed in the range of approximately three-fourths of the distance from the juncture of the upper right edge 106 and the lower right edge 102 and the juncture of the lower right edge 102 and the bottom edge 110.

Figure 3:
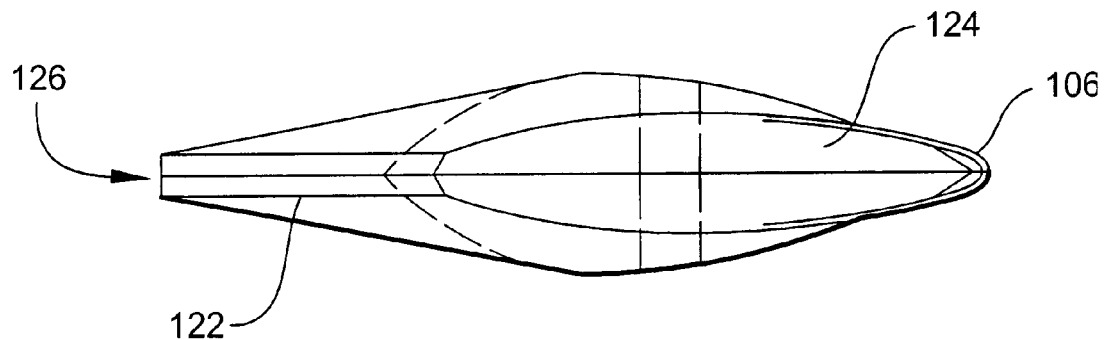
FIG. 3 is a cross section of the invention at line 3—3 of FIG. 2.
Figure 4:
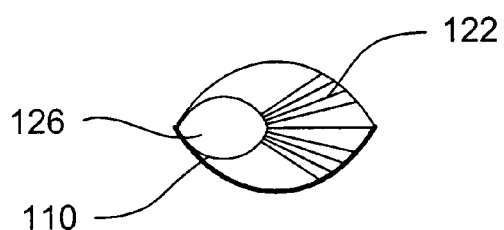
FIG. 4 is a cross section of the invention at line 4—4 of FIG. 2.
Figure 5:
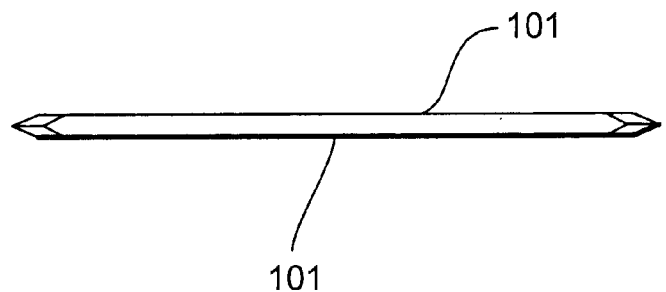
FIG. 5 is a cross section of the invention at line 5—5 of FIG. 1.

FIG. 3 presents a cross section, from above, of open cone 100 at line 3—3 of FIG. 2, while FIG. 4 presents a cross section, from above, at line 4—4 of FIG. 2. FIG. 5 presents a cross section of the folded invention at line 5—5 of FIG. 1.

Figure 6:
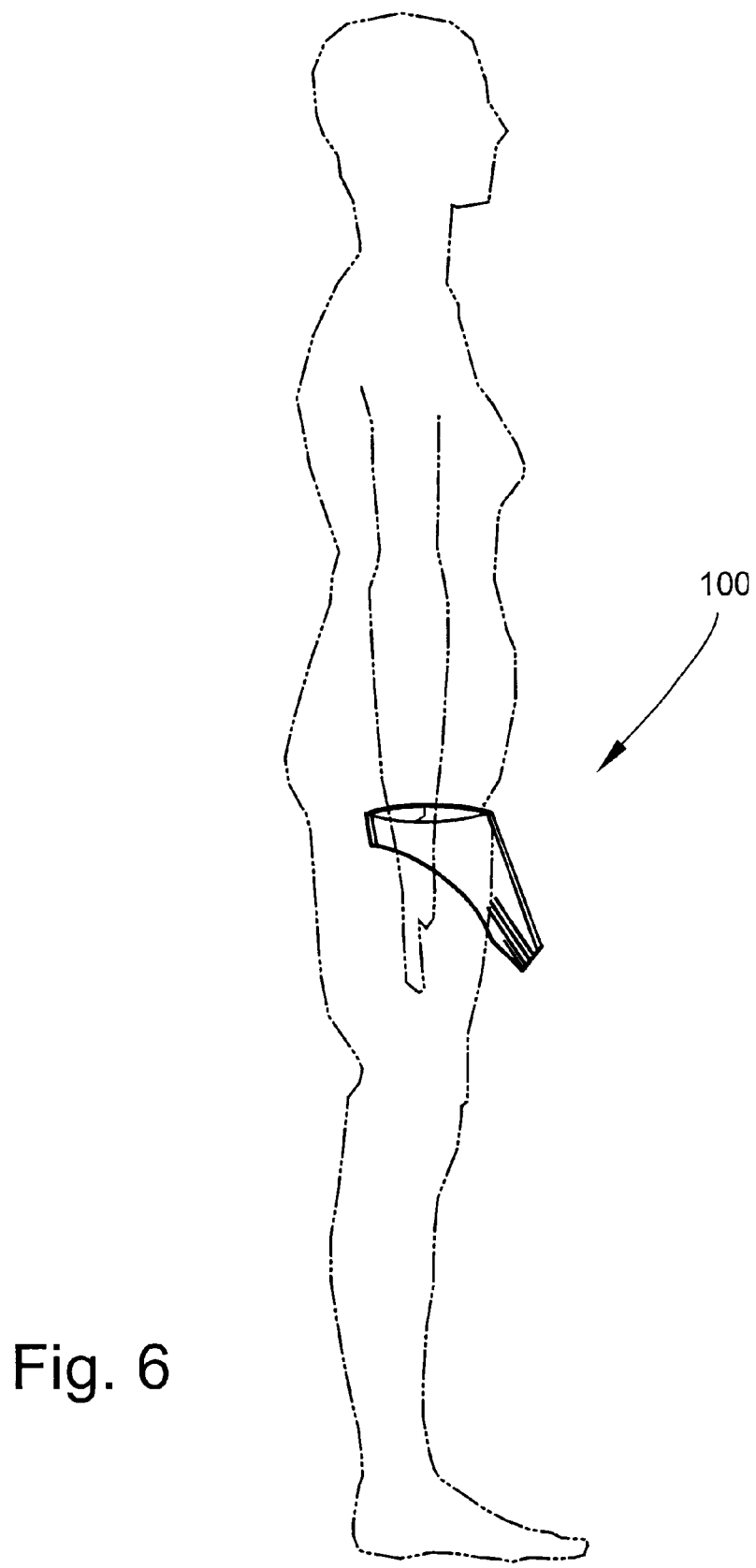
FIG. 6 is an illustration of the invention in its intended environment.

As illustrated in FIG. 6, a woman may use the device in a standing position allowing her to direct the flow of urine away from her body by cupping her vulva within the upper opening and pointing the lower opening away from herself.

It would be evident to one skilled in the art that the present invention could be produced of a number of different materials and that the size and shape could be varied without affecting its unique ability to retain its shape when pressed into its open position.

It is to be understood that the present invention is not limited to the embodiments described above, but encompasses any and all embodiments within the scope of the following claims.

I claim:

1. A device to facilitate female urination from a standing position, comprising:

a) a pair of substantially planar pentagonal sides, each having a top edge, a bottom edge, an upper right edge, a lower right edge and a left edge, said pair of sides being continuously joined one to the other along said upper right edge, said lower right edge and said left edge, thereby defining an upper right, a lower right and a left hinge line, respectively, said pair of sides being disposed substantially flat and adjacent one another for storage and being movable away from one another to an open, operable position; and b) means for releasably locking said pair of sides in said open, operable position hingedly connected along said lower right hinge line;

said open, operable position defining a hollow structure having a semi-elliptical opening proximate said top edge of said pair of sides adapted to enclose a female users vulva for receiving urine, and a lower opening proximate said bottom edges of said pair of sides for discharging urine.

2. The device to facilitate female urination from a standing position as recited in claim 1, wherein said substantially pentagonal shape is configured such that said lower opening for discharging urine is oriented such that discharged urine is directed away from the body of a user.

3. The device to facilitate female urination from a standing position as recited in claim 1, wherein said semi-elliptical opening proximate said top edge of said pair of sides comprises a finished edge.

4. The device to facilitate female urination from a standing position as recited in claim 3, wherein said finished edge comprises a flap folded inwardly.

5. The device to facilitate female urination from a standing position as recited in claim 1, wherein said locking means comprises a semi-elliptical scored line disposed in each of said pair of sides, said scored lines having a first terminus proximate a juncture of said upper right edge and said lower right edge and a second terminus located along said lower right edge.

6. The device to facilitate female urination from a standing position as recited in claim 5, wherein said second terminus is disposed in the range of approximately three-fourths of the distance from said juncture of said upper right edge and said lower right edge and the juncture of said lower right edge and said bottom edge.

7. The device to facilitate female urination from a standing position as recited in claim 1, further comprising:

at least one score line disposed in each of said pair of sides, said at least one score line running from a central region of and substantially perpendicular to said bottom edge of said pair of sides.

8. The device to facilitate female urination from a standing position as recited in claim 1, wherein said pair of sides comprise water resistant paper.

9. The device to facilitate female urination from a standing position as recited in claim 8, wherein said device is intended for multiple uses.

10. A method for using an apparatus to facilitate female urination from a standing position, the steps comprising:

a) providing a urination aid comprising a pair of substantially planar pentagonal sides, each having a top edge, a bottom edge, an upper right edge, a lower right edge and a left edge, said pair of sides being continuously joined one to the other along said upper right edge, said lower right edge and said left edge, thereby defining an upper right, a lower right and a left hinge line, respectively, said pair of sides being disposed substantially flat and adjacent one another for storage and being movable away from one another to an open, operable position; and means for releasably locking said pair of sides in said open, operable position hingedly connected along said lower right hinge line; said open, operable position defining a hollow structure having a semi-elliptical opening proximate said top edge of said pair of sides, said opening being adapted to enclose a female users vulva for receiving urine, and a lower opening proximate said bottom edges of said pair of sides for discharging urine;

b) opening said urination aid by exerting pressure to a central point on said lower right edge and a predetermined point on said left edge, applying sufficient pressure to lock said urination aid in said open, operable position;

c) placing said semi-elliptical opening proximate said top edge of said pair of sides proximate the vulva of a user so as to substantially enclose said vulva;

d) orienting said lower opening proximate said bottom edges of said pair of sides in a desired direction; and e) urinating.

11. The method for using an apparatus to facilitate female urination from a standing position as recited in claim 10, the steps further comprising:

f) collapsing said urination aid; and g) disposing of said urination aid.

12. The method for using an apparatus to facilitate female urination from a standing position as recited in claim 10, the steps further comprising:

f) cleaning said urination aid;

g) collapsing said urination aid; and h) storing said urination aid.

* * * * *